United States Patent
Lutzen et al.

(10) Patent No.: US 9,898,581 B2
(45) Date of Patent: *Feb. 20, 2018

(54) HEALTH CARE ELIGIBILITY VERIFICATION AND SETTLEMENT SYSTEMS AND METHODS

(71) Applicant: First Data Corporation, Greenwood Village, CO (US)

(72) Inventors: Renee Elahi Lutzen, Omaha, NE (US); George Nauman, Omaha, NE (US); David G. Weis, Omaha, NE (US); Beverly Kennedy, Greenwood Village, CO (US); Robyn Bartlett, Omaha, NE (US)

(73) Assignee: First Data Corporation, Greenwood Village, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/257,784

(22) Filed: Apr. 21, 2014

(65) Prior Publication Data

US 2014/0316798 A1 Oct. 23, 2014

Related U.S. Application Data

(63) Continuation of application No. 11/153,218, filed on Jun. 14, 2005, now Pat. No. 8,751,250, which is a
(Continued)

(51) Int. Cl.
| | |
|---|---|
| *G06Q 50/22* | (2012.01) |
| *G06Q 20/10* | (2012.01) |
| *G06F 19/00* | (2018.01) |
| *G06Q 10/00* | (2012.01) |
| *G07G 1/00* | (2006.01) |
| *G07G 1/12* | (2006.01) |

(52) U.S. Cl.
CPC .......... *G06F 19/327* (2013.01); *G06F 19/328* (2013.01); *G06Q 10/00* (2013.01);
(Continued)

(58) Field of Classification Search
CPC ....... G06Q 50/22; G06Q 20/10; G06F 19/323
(Continued)

(56) References Cited

U.S. PATENT DOCUMENTS

| | | |
|---|---|---|
| 3,599,151 A | 8/1971 | Harr |
| 3,833,395 A | 9/1974 | Gosnell |

(Continued)

FOREIGN PATENT DOCUMENTS

| | | |
|---|---|---|
| EP | 0481135 A1 | 4/1992 |
| EP | 0949596 A2 | 10/1999 |

(Continued)

OTHER PUBLICATIONS

Chico Research Foundation (CSU), Personal Physician Pre-Designation for Work Related Injuries or Illness, Feb. 1, 2001, pp. 1-6.*
(Continued)

*Primary Examiner* — Joy Chng
(74) *Attorney, Agent, or Firm* — Kilpatrick Townsend & Stockton LLP

(57) ABSTRACT

Devices, systems, and methods for processing healthcare and financial transactions are provided. A point-of-care terminal for processing a healthcare transaction by a healthcare provider includes a reader configured to read information from a healthcare eligibility and settlement presentation instrument associated with a patient, and a processor configured to process a healthcare transaction based on the information, wherein the healthcare transaction includes at least one of a healthcare eligibility verification transaction and a healthcare settlement transaction.

15 Claims, 13 Drawing Sheets

Related U.S. Application Data continuation-in-part of application No. 10/846,947, filed on May 13, 2004, now abandoned, said application No. 11/153,218 is a continuation-in-part of application No. 10/460,741, filed on Jun. 11, 2003, now Pat. No. 8,086,539, said application No. 10/846,947 is a continuation-in-part of application No. 10/675,929, filed on Sep. 29, 2003, now abandoned.

(60) Provisional application No. 60/515,918, filed on Oct. 29, 2003, provisional application No. 60/388,047, filed on Jun. 11, 2002, provisional application No. 60/417,205, filed on Oct. 8, 2002.

(52) U.S. Cl.
CPC ........... *G06Q 50/22* (2013.01); *G07G 1/0018* (2013.01); *G07G 1/12* (2013.01); *G06F 19/323* (2013.01)

(58) Field of Classification Search
USPC .................................................. 705/2–3
See application file for complete search history.

(56) References Cited

U.S. PATENT DOCUMENTS

| | | | |
|---|---|---|---|
| 4,321,672 | A | 3/1982 | Braun et al. |
| 4,491,725 | A | 1/1985 | Pritchard |
| 4,562,340 | A | 12/1985 | Tateisi et al. |
| 4,562,341 | A | 12/1985 | Ohmae et al. |
| 4,630,200 | A | 12/1986 | Ohmae et al. |
| 4,678,895 | A | 7/1987 | Tateisi et al. |
| 4,722,554 | A | 2/1988 | Pettit |
| 4,812,628 | A | 3/1989 | Boston et al. |
| 4,961,142 | A | 10/1990 | Elliott et al. |
| 5,070,452 | A | 12/1991 | Doyle et al. |
| 5,119,293 | A | 6/1992 | Hammond |
| 5,175,682 | A | 12/1992 | Higashiyama et al. |
| 5,220,501 | A | 6/1993 | Lawlor et al. |
| 5,221,838 | A * | 6/1993 | Gutman ............... G06Q 20/32 235/379 |
| 5,283,829 | A | 2/1994 | Anderson |
| 5,367,452 | A | 11/1994 | Gallery et al. |
| 5,408,077 | A | 4/1995 | Campo et al. |
| 5,426,594 | A | 6/1995 | Wright et al. |
| 5,464,971 | A | 11/1995 | Sutcliffe et al. |
| 5,484,988 | A | 1/1996 | Hills et al. |
| 5,491,325 | A | 2/1996 | Huang et al. |
| 5,504,677 | A | 4/1996 | Pollin |
| 5,510,979 | A | 4/1996 | Moderi et al. |
| 5,555,496 | A | 9/1996 | Tackbary et al. |
| 5,577,109 | A | 11/1996 | Stimson et al. |
| 5,578,808 | A * | 11/1996 | Taylor ................. G06Q 20/02 235/375 |
| 5,590,038 | A * | 12/1996 | Pitroda ................ G06Q 20/02 235/380 |
| 5,622,388 | A | 4/1997 | Alcordo |
| 5,657,201 | A | 8/1997 | Kochis |
| 5,677,955 | A | 10/1997 | Doggett et al. |
| 5,679,940 | A | 10/1997 | Templeton et al. |
| 5,699,528 | A | 12/1997 | Hogan |
| 5,748,737 | A * | 5/1998 | Daggar ................ G06K 7/0021 235/379 |
| 5,757,917 | A | 5/1998 | Rose et al. |
| 5,794,207 | A | 8/1998 | Walker et al. |
| 5,815,657 | A | 9/1998 | Williams et al. |
| 5,826,241 | A | 10/1998 | Stein et al. |
| 5,828,875 | A | 10/1998 | Halvarsson et al. |
| 5,832,447 | A | 11/1998 | Rieker et al. |
| 5,832,463 | A | 11/1998 | Funk |
| 5,893,080 | A | 4/1999 | McGurl et al. |
| 5,910,988 | A | 6/1999 | Ballard |
| 5,940,811 | A | 8/1999 | Norris |
| 5,949,044 | A | 9/1999 | Walker et al. |
| 5,956,700 | A | 9/1999 | Landry |
| 5,960,412 | A | 9/1999 | Tackbary et al. |
| 5,987,426 | A | 11/1999 | Goodwin, III |
| 5,987,429 | A | 11/1999 | Maritzen et al. |
| 5,995,965 | A * | 11/1999 | Experton ............ G06F 19/322 707/959 |
| 6,012,035 | A | 1/2000 | Freeman et al. |
| 6,029,150 | A | 2/2000 | Kravitz |
| 6,030,000 | A | 2/2000 | Diamond |
| 6,032,133 | A | 2/2000 | Hilt et al. |
| 6,032,137 | A | 2/2000 | Ballard |
| 6,039,245 | A | 3/2000 | Symonds et al. |
| 6,044,360 | A | 3/2000 | Picciallo |
| 6,058,417 | A | 5/2000 | Hess et al. |
| 6,064,990 | A | 5/2000 | Goldsmith |
| 6,070,798 | A | 6/2000 | Nethery |
| 6,097,834 | A | 8/2000 | Krouse et al. |
| 6,106,020 | A | 8/2000 | Leef et al. |
| 6,108,641 | A | 8/2000 | Kenna et al. |
| 6,119,106 | A | 9/2000 | Mersky et al. |
| 6,122,625 | A | 9/2000 | Rosen |
| 6,164,528 | A | 12/2000 | Hills et al. |
| 6,175,823 | B1 | 1/2001 | Van Dusen |
| 6,193,152 | B1 | 2/2001 | Fernando et al. |
| 6,199,761 | B1 | 3/2001 | Drexler |
| 6,208,973 | B1 * | 3/2001 | Boyer .................. G06Q 20/02 705/2 |
| 6,230,201 | B1 | 5/2001 | Guck et al. |
| 6,246,996 | B1 | 6/2001 | Stein et al. |
| 6,305,604 | B1 | 10/2001 | Ono |
| 6,308,887 | B1 | 10/2001 | Korman et al. |
| 6,308,890 | B1 | 10/2001 | Cooper |
| 6,327,575 | B1 | 12/2001 | Katz |
| 6,360,254 | B1 | 3/2002 | Linden et al. |
| 6,367,693 | B1 | 4/2002 | Novogrod |
| 6,405,176 | B1 | 6/2002 | Toohey |
| 6,453,297 | B1 | 9/2002 | Burks et al. |
| 6,453,306 | B1 | 9/2002 | Quelene |
| 6,473,740 | B2 | 10/2002 | Cockrill et al. |
| 6,484,936 | B1 | 11/2002 | Nicoll et al. |
| 6,516,302 | B1 | 2/2003 | Deaton et al. |
| 6,539,363 | B1 | 3/2003 | Allgeier et al. |
| 6,547,132 | B1 | 4/2003 | Templeton et al. |
| 6,827,260 | B2 | 12/2004 | Stoutenburg et al. |
| 6,886,742 | B2 | 5/2005 | Stoutenburg et al. |
| 7,174,302 | B2 | 2/2007 | Patricelli et al. |
| 2001/0037361 | A1 | 11/2001 | Croy |
| 2001/0051876 | A1 | 12/2001 | Seigel et al. |
| 2001/0056379 | A1 | 12/2001 | Fujunaga et al. |
| 2002/0116324 | A1 | 8/2002 | Macias |
| 2002/0138363 | A1 | 9/2002 | Karas et al. |
| 2002/0139849 | A1 * | 10/2002 | Gangi .................. G06Q 20/00 235/440 |
| 2002/0152179 | A1 | 10/2002 | Racov |
| 2002/0153414 | A1 | 10/2002 | Stoutenburg et al. |
| 2002/0174020 | A1 | 11/2002 | Grey et al. |
| 2002/0188467 | A1 * | 12/2002 | Eke .................... G06F 19/3418 705/2 |
| 2003/0111529 | A1 | 6/2003 | Templeton et al. |
| 2003/0189782 | A1 | 10/2003 | Leonhardt et al. |
| 2003/0222135 | A1 | 12/2003 | Stoutenburg et al. |
| 2004/0039693 | A1 | 2/2004 | Nauman et al. |
| 2004/0148203 | A1 | 7/2004 | Whitaker et al. |
| 2005/0015280 | A1 | 1/2005 | Gabel et al. |
| 2005/0125258 | A1 | 6/2005 | Yellin et al. |

FOREIGN PATENT DOCUMENTS

| | | |
|---|---|---|
| EP | 1077436 A2 | 2/2001 |
| WO | 0046725 A1 | 8/2000 |
| WO | 0067177 | 11/2000 |
| WO | 0104816 | 1/2001 |
| WO | 0205195 A1 | 1/2002 |

OTHER PUBLICATIONS

Chico Research Foundation (CSU), Personal Physician Pre-Designation for Work Related Injuries or Illness, Feb. 1, 2001.*
U.S. Appl. No. 11/153,218, filed Jun. 14, 2005, all pages.

(56) References Cited

OTHER PUBLICATIONS

"Gemplus: Secure Management of Medical and Administrative Data," obtained from website http://web.archive.org/web/20010609222540/www.gemplus.com/app/health/index.htm on Aug. 1, 2007, 20 pages.

"MCI to Provide Backbone for Smart Card Health Care Claims Processing," *Communications Today*, Potomac: Dec. 11, 1997, 2 pages.

Arthas Corp., "dotBank, The Way to Send and Receive Money on the Internet," downloaded from website dotbank.com on Feb. 7, 2000.

Business Wire, "E-Commerce, Email and E-greeting Cards Combine in New Web Site Designed by Interactive Bureau", Sep. 14, 1999 (abstract), [online] [retrieved on May 1, 2002], retrieved from PROQUEST Database, 2 pages.

Confinity, Inc., "PayPal.com, How PayPal.com Works," download from website http://www.paypal.com on Feb. 7, 2000, 7 pages.

Idealab Company, "PayMe.com," download from website http://ssl.idealab.com on Feb. 16, 2000, 7 pages.

Maxey, Brigitte, "New Card to Aid the Sick Onecard will store health, credit data," *The Sun*, Baltimore, MD: Dec. 16, 1991, 2 pages.

PR Newswire, "GiftSpot.com Simplifies Gift-Giving on the Internet," Oct. 20, 1990 (abstract), [online] retrieved on May 1, 2002], retrieved from PROQUEST Database, 5 pages.

Tranz 330 Fast, "Low-Cost Transaction Automation At the Point of Service," http://www.vfifinance.com/tranz330.htm, VeriForne Finance, pp. 1-3, especially pp. 1-2, Jan. 1999.

x.com, "Do More with Your Money," download from website http://www.x.com., 5 pages, Feb. 7, 2000.

\* cited by examiner

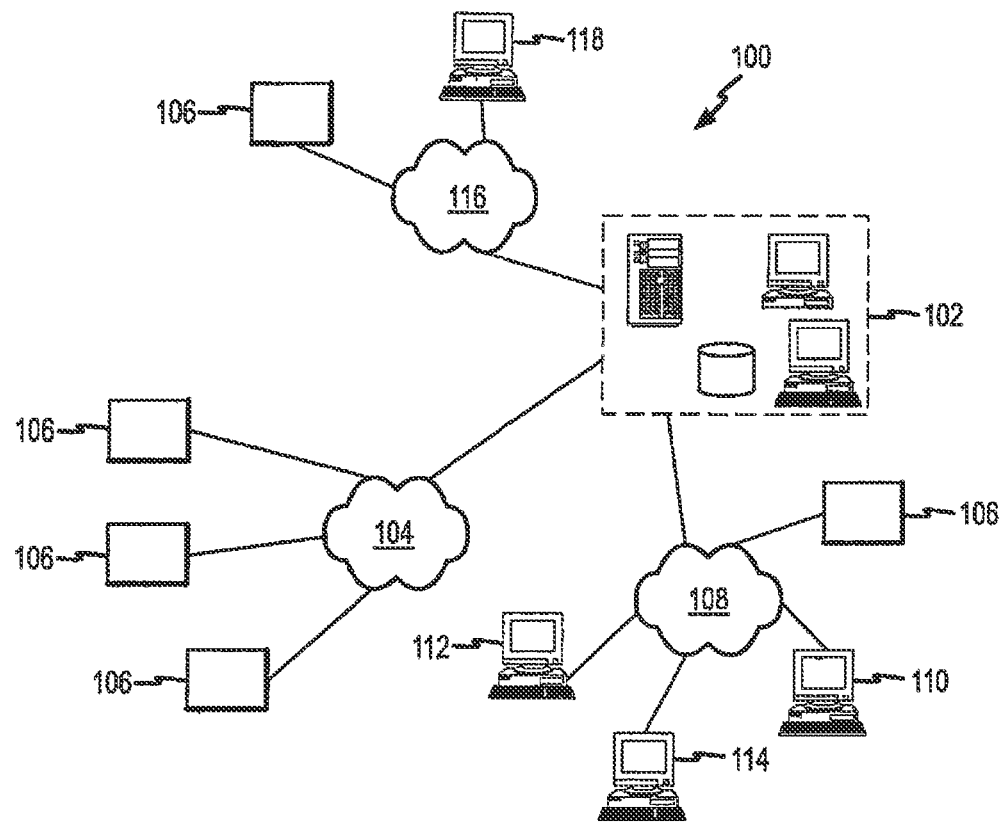
FIG.1A
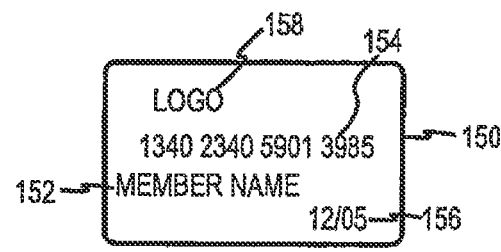
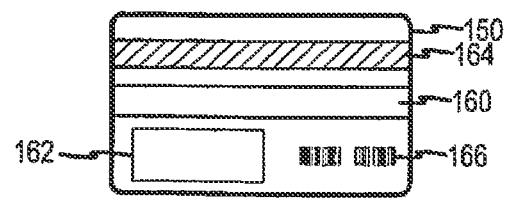
FIG.1B

| 300 | ELIGIBILITY | | |
|---|---|---|---|
| 302 | PRESS CANCEL | 304 | MMDDYY HH:MM<br>SELECT SERVICE<br>FINANCIAL HEALTHCARE |
| 306 | SELECT HEALTHCARE | 308 | SELECT SERVICE<br>ELIGIBILITY REPORT<br>RESET |
| 310 | SELECT ELIGIBILITY | 312 | SWIPE PATIENT CARD<br>OR ENTER PAYER ID |
| 314 | SWIPE CARD OR KEY PAYER ID<br>PRESS ENTER | 316 | ENTER PROVIDER ID |
| 318 | KEY PROVIDER ID<br>PRESS ENTER | 320 | SELECT PATIENT TYPE<br>SELF CHILD<br>SPOUSE OTHER |
| 322 | SELECT DESIRED OPTION | 324 | ENTER PATIENT DOB<br>(MMDDYYYY):____ |
| 326 | KEY PATIENT DOB<br>(IN MMDDYYYY FORMAT)<br>PRESS ENTER | 328 | ENTER DATE OF SERVICE<br>(MMDDYYYY):____ |
| 330 | KEY DATE OF SERVICE<br>(IN MMDDYYYY FORMAT)<br>PRESS ENTER | 332 | ENTER POLICY/GROUP # |
| 334 | KEY POLICY/GROUP #<br>PRESS ENTER | 336 | ENTER SUBSCRIBER ID # |
| 338 | KEY SUBSCRIBER ID #<br>PRESS ENTER | 340 | FIRST NAME:____ |
| 342 | KEY SUBSCRIBER FIRST NAME<br>PRESS ENTER | 344 | LAST NAME:____ |
| 346 | KEY SUBSCRIBER LAST NAME<br>PRESS ENTER | 348 | (HOST COMMUNICATION) |
| | | 350 | PRINTING......PLEASE WAIT |
| | | 352 | ELIGIBILITY COMPLETE<br>REPRINT RECEIPT<br><YES> <NO> |
| 354 | SELECT DESIRED OPTION | 352 | ELIGIBILITY COMPLETE<br>REPRINT RECEIPT<br><YES> <NO> |
| 356 | PRESS CANCEL 2X TO EXIT | 358 | IDLE PROMPT |

FIG.3

| (300a) | ELIGIBILITY | (Payer in Network) |
|---|---|---|
| 302a<br>PRESS CANCEL | 304a<br>MMDDYY HH:MM<br>SELECT SERVICE<br>FINANCIAL HEALTHCARE |
| SELECT HEALTHCARE | SELECT SERVICE<br>ELIGIBILITY REPORT<br>RESET |
| SELECT ELIGIBILITY | SWIPE PATIENT CARD<br>OR ENTER PAYER ID |
| 314a<br>SWIPE CARD OR KEY PAYER ID<br>PRESS ENTER | 316a<br>ENTER PROVIDER ID (DOCTOR)<br>OR PRESS MENU |
| 318a<br>KEY PROVIDER ID and PRESS ENTER<br>OR PRESS MENU | 320a<br>Provider No.   Provider Name   Provider ID<br>01   Dr. Smith   0123445<br>02   Dr. Black   2344556<br>03   Dr. Jones   4455667<br>04   Dr. Green   5666788 |
| 322a<br>KEY PROVIDER NO.<br>OR SELECT PROVIDER NAME<br>PRESS ENTER | 324a<br>PATIENT TYPE<br>SPOUSE   SELF   CHILD<br>OTHER |
| 326a<br>SELECT DESIRED OPTION | |

FIG. 3A

| (300b) | ELIGIBILITY | | (Payer not in Network) |
|---|---|---|---|
| | PRESS CANCEL | | MMDDYY      HH:MM <br> SELECT SERVICE <br> FINANCIAL      HEALTHCARE |
| | SELECT HEALTHCARE | | SELECT SERVICE <br> ELIGIBILITY      REPORT <br> RESET |
| | SELECT ELIGIBILITY | | SWIPE PATIENT CARD, <br> ENTER PAYER ID, <br> OR PRESS MENU KEY |
| 314b | SWIPE CARD, <br> KEY PAYER ID and PRESS ENTER <br> OR PRESS MENU | 316b | Table No.    Payer Name    Payer No. <br> 01        BC Inc.        0123445 <br> 02        ATNA Inc.     2344556 <br> 03        CGNA Co.     4455667 <br> 04        AV Inc.        5666788 |
| 318b | KEY PAYER TABLE NO. <br> OR SELECT PAYER NAME <br> PRESS ENTER | 320b | ENTER PROVIDER ID (DOCTOR) <br> OR PRESS MENU |
| 322b | KEY PROVIDER ID and PRESS ENTER <br> OR PRESS MENU | 324b | Provider No.    Provider Name    Provider Taxpayer ID <br> 01          Dr. Smith       3456445 <br> 02          Dr. Black       2341236 <br> 03          Dr. Jones       4412367 <br> 04          Dr. Green      5898888 |
| 326b | KEY PROVIDER NO. <br> OR SELECT PROVIDER NAME <br> PRESS ENTER | 328b | ENTER POLICY/GROUP # |
| 330b | KEY POLICY/GROUP # <br> PRESS ENTER | 332b | ENTER SUBSCRIBER ID # |
| 334b | KEY SUBSCRIBER ID # <br> PRESS ENTER | | |

FIG. 3B

| (300c) | ELIGIBILITY | | (No Card) |
|---|---|---|---|
| PRESS CANCEL | | MMDDYY      HH:MM <br> SELECT SERVICE <br> FINANCIAL     HEALTHCARE | |
| SELECT HEALTHCARE | | SELECT SERVICE <br> ELIGIBILITY     REPORT <br> RESET | |
| SELECT ELIGIBILITY | | CALL FOR AUTHORIZATION, <br> ENTER PAYER ID, <br> OR PRESS MENU KEY | |
| KEY PAYER ID and PRESS ENTER <br> OR PRESS MENU | | Table No.    Payer Name    Payer No. <br> 01           Dr. Smith      0123445 <br> 02           Dr. Black      2344556 | |
| KEY PAYER NO. <br> PRESS ENTER | | 320c <br> ENTER PROVIDER ID (DOCTOR) <br> OR PRESS MENU | |
| KEY PROVIDER ID and PRESS ENTER <br> OR PRESS MENU | | Provider No.    Provider Name    Provider Taxpayer ID <br> 01            BC Inc.           012134545 <br> 02            ATNA Inc.       908762344556 | |
| KEY PROVIDER NO. <br> PRESS ENTER | | 328c <br> ENTER POLICY/GROUP # | |
| 330c <br> KEY POLICY/GROUP # <br> PRESS ENTER | | 332c <br> ENTER SUBSCRIBER ID # | |
| 334c <br> KEY SUBSCRIBER ID # <br> PRESS ENTER | | FIRST NAME:_____ | |
| KEY PATIENTS FIRST NAME <br> PRESS ENTER | | MIDDLE NAME:_____ | |
| KEY PATIENTS MIDDLE NAME <br> PRESS ENTER | | LAST NAME:_____ | |
| KEY PATIENTS LAST NAME <br> PRESS ENTER | | | |

FIG. 3C

400a  ACCEPTED ELIGIBILITY RECEIPT

```
                    THE MEDICAL CENTER
                    123 MAIN STREET
                    ANYTOWN, USA
TERMINAL ID. NO.:                                    123456799
DATE: FEBRUARY 8, 2005                         TIME: 11:36AM

ELIGIBILITY TRACE: 00028
EFFECTIVE DATE: 02082005

PROVIDER NAME/ID: 0011223344
PAYER: 12345
GROUP/POLICY #: ABC12334

SUBSCRIBER ID: 4AB59832476
SUBSCRIBER NAME/ADDRESS: JANE DOE, 456 1ST AVE., ANYTOWN, USA
PATIENT: CHILD (JILL DOE)
PATIENT DOB: 07141998

HEALTH BENEFIT PLAN COVERAGE
ELIGIBILITY: ACTIVE
COVERAGE: FAMILY
INS. TYPE: HEALTH MAINTENANCE ORGANIZATION

CO-PAY IN-NET INDIVIDUAL
   $0.00 FACILITY IP HOSPITAL
   $0.00 HOSPITAL - O/P SURGERY
  $10.00 PCP AFTER HOURS
   $5.00 PCP DURING HOURS
CO-PAY IN-NET INDIVIDUAL/DAY
   $0.00 FACILITY OP DIAGNOSTIC TESTING
   $0.00 FACILITY OP LAB
   $0.00 FACILITY OP XRAY
   $5.00 SPECIALIST OFF VISIT CONSULT
CO-PAY IN-NET INDIVIDUAL/ADMISSION
  $25.00 HOSPITAL EMERGENCY

PRIMARY CARE PHYSICIAN (PCP)
PCP NAME: DR. JACKIE SPECIALIST, MD
TELEPHONE: 111-555-1255
PCP
GREAT PROVIDER
1 COPAY/SVC BASED ON PROV TYPE
1 COINS/SVC BASED ON PROV TYPE
```

FIG.4A

400b ACCEPTED ELIGIBILITY RECEIPT WITH CO-PAY INFORMATION FROM PAYER

```
                         THE MEDICAL CENTER
                          123 MAIN STREET
                          ANYTOWN, USA
TERMINAL ID. NO.:                                       123456799
DATE: FEBRUARY 8, 2005                              TIME: 11:36AM

ELIGIBILITY TRACE: 00028
EFFECTIVE DATE: 02082005

PROVIDER NAME/ID: 0011223344
PAYER: 12345
GROUP/POLICY #: ABC12334

SUBSCRIBER ID: 4AB59832476
SUBSCRIBER NAME/ADDRESS: JANE DOE, 456 1ST AVE., ANYTOWN, USA
PATIENT: CHILD (JIM DOE)
PATIENT DOB: 07141995

HEALTH BENEFIT PLAN COVERAGE
ELIGIBILITY: ACTIVE
COVERAGE: FAMILY
INS. TYPE: HEALTH MAINTENANCE ORGANIZATION

CO-PAY IN-NET INDIVIDUAL
   $300.00 FACILITY IP HOSPITAL
   $300.00 HOSPITAL - O/P SURGERY
   $25.00 PCP AFTER HOURS
   $25.00 PCP DURING HOURS
CO-PAY IN-NET INDIVIDUAL/DAY
   $35.00 FACILITY OP DIAGNOSTIC TESTING
   $35.00 FACILITY OP LAB
   $35.00 FACILITY OP XRAY
   $35.00 SPECIALIST OFF VISIT CONSULT
CO-PAY IN-NET INDIVIDUAL/ADMISSION
   $100.00 HOSPITAL EMERGENCY

PRIMARY CARE PHYSICIAN (PCP)
PCP NAME: THE FAMILY CLINIC AND MEDICAL CENTER
TELEPHONE: 111-555-1234
PROVIDER
* 1 COPAY/SVC BASED ON PROV TYPE
* NO NON-EMERGENCY COVG OON
* APPLIES ONLY TO PAYER HMO PROV
```
* DYNAMIC TEXT - DEPENDENT ON WHAT PAYER SENDS BACK IN THE 271

FIG.4B

400c                    REJECTED ELIGIBILITY RECEIPT

```
                        THE MEDICAL CENTER
                         123 MAIN STREET
                          ANYTOWN, USA
TERMINAL ID. NO.:                                        123456799
DATE: FEBRUARY 8, 2005                              TIME: 11:36AM

ELIGIBILITY TRACE: 00028
EFFECTIVE DATE: 02082005

PROVIDER NAME/ID: 0011223344
PAYER: 12345
GROUP/POLICY #: ABC12334

SUBSCRIBER ID: 459832476
SUBSCRIBER NAME/ADDRESS: JOHN DOE, 456 1ST AVE., ANYTOWN, USA
PATIENT: SELF
PATIENT DOB: 07141967

REQUEST VALID
REJECT REASON: PATIENT NOT FOUND
ACTION: PLEASE CORRECT AND RESUBMIT
```

FIG.4C

| (500) | RESET HEALTHCARE BATCH | | |
|---|---|---|---|
| 502<br>PRESS CANCEL | | 504<br>MMDDYY      HH:MM<br>SELECT SERVICE<br>FINANCIAL      HEALTHCARE | | |
| 506<br>SELECT HEALTHCARE | | 508<br>SELECT SERVICE<br>ELIGIBILITY      REPORT<br>RESET | | |
| 510<br>SELECT RESET | | 512<br>DO YOU WANT TO PRINT<br>THE ELIGIBILITY TOTALS?<br><YES>      <NO> | | |
| 514<br>PRESS DESIRED OPTIONS | | 516<br>PRINTING REPORT<br>PLEASE WAIT...... | | |
| 518<br>PRESS CANCEL TO EXIT | | 520<br>IDLE PROMPT | | |

FIG. 5

| (600) | PRINT HEALTHCARE REPORT | | |
|---|---|---|---|
| PRESS CANCEL | | 604<br>MMDDYY      HH:MM<br>SELECT SERVICE<br>FINANCIAL      HEALTHCARE | | |
| 606<br>SELECT HEALTHCARE | | 608<br>SELECT SERVICE<br>ELIGIBILITY      REPORT<br>RESET | | |
| 610<br>SELECT REPORT | | 612<br>PRINTING REPORT<br>PLEASE WAIT...... | | |
| | | 604<br>MMDDYY      HH:MM<br>SELECT SERVICE<br>FINANCIAL      HEALTHCARE | | |

FIG. 6

HEALTH CARE ELIGIBILITY VERIFICATION AND SETTLEMENT SYSTEMS AND METHODS

CROSS-REFERENCES TO RELATED APPLICATIONS

This application is a continuation of U.S. patent application Ser. No. 11/153,218, filed Jun. 14, 2005, which is a continuation-in-part of U.S. patent application Ser. No. 10/846,947, filed May 13, 2004 ; which claims the benefit under 35 USC 119(e) of U.S. Provisional Patent Application No. 60/515,918, filed Oct. 29, 2003 ; and which is a continuation-in-part of U.S. patent application Ser. No. 10/460,741, filed Jun. 11, 2003 , which claims the benefit under 35 USC 119(e) of U.S. Provisional Patent Application No. 60/388,047, filed Jun. 11, 2002 ; and which is a continuation-in-part of U.S. patent application Ser. No. 10/675,929, filed Sep. 29, 2003 , which claims the benefit of U.S. Provisional Patent Application No. 60/417,205, filed Oct. 8, 2002.

This application is related to U.S. patent application Ser. No. 10/116,289, filed Apr. 3, 2002 , which is a continuation-in-part of U.S. patent application Ser. No. 09/634,901, filed Aug. 9, 2000 , which claims the benefit under 35 USC 119(e) of U.S. Provisional Patent Application No. 60/147,899, filed Aug. 9, 1999 . Further, this application is related to U.S. patent application Ser. No. 10/116,733, filed Apr. 3, 2002 , U.S. patent application Ser. No. 10/116,686, filed Apr. 3, 2002, now U.S. Pat. No. 6,827,260 , U.S. patent application Ser. No. 10/116,735, filed Apr. 3, 2002 , and U.S. patent application Ser. No. 10/358,615, filed Feb. 5, 2003 . This application is also related to U.S. patent application Ser. No. 11/100,327, filed Apr. 5, 2005 . The entire disclosure of each of the above filings is herein incorporated by reference for all purposes.

BACKGROUND OF THE INVENTION

The present invention relates to the processing of insurance-related information. More particularly, the present invention relates to point-of-care devices, methods, and systems for verifying insurance eligibility and handling settlement transactions.

The process for health care providers to verify a patient's insurance eligibility and to settle claims is ripe for improvement. Prior to providing care, providers typically contact payers to verify whether a patient is actually covered under a particular plan, what specific procedures, lab tests, and the like are covered under the plan, and whether dependents are covered. In most present cases, providers either type patient information into a web-based or batch-based system or call voice IVR (interactive voice response) systems to verify a patient's coverage. Once eligibility is verified, the co-pay amount may be determined and the patient may be expected to make payment prior to receiving care. This often requires the provider to process a financial transaction through a separate procedure. This process is costly, time consuming, and error prone, often resulting in delayed payment of claims due to eligibility issues.

Once care is provided, providers often file claims on behalf of patients and await payment from the coverage provider. If the patient paid a deductible, co-payment, or an initial or other payment, the patient also may complete claim forms and return them to a provider or third party administrator. Further, if the patient received a prescription from the doctor, the patient and/or a pharmacist also may complete claim forms for reimbursement for pharmaceuticals and/or over-the-counter medications, which, in some cases, are now reimbursable under flexible spending accounts (FSAs), health reimbursement accounts (HRAs) and/or other types of healthcare and/or stored value balances. Each of these processes is administratively intensive; collectively they become overwhelming for some individuals for even a single doctor visit.

For the foregoing reasons, there is a need for a point-of-care insurance eligibility verification and settlement terminal and methods of using such. Hence, among a number of other advantages apparent from the following description, the present invention addresses these and other issues related to health care eligibility verification and settlement by providing systems, devices, and methods for addressing the aforementioned limitations.

BRIEF SUMMARY OF THE INVENTION

The present invention provides healthcare terminal devices that allow a doctor or other provider to obtain insurance coverage information for a patient, process information for a claim adjudication, receive payment for services from a patient's credit card and/or FSA, and obtain prescription information for the patient.

In a first aspect, the present invention provides a point-of-care device having a base unit adapted for performing healthcare functions at a point-of-care. The base unit can include a base unit housing and a processor disposed within the base unit housing. The processor can be configured to process a plurality of transaction types. One of the plurality of transaction types can be a healthcare insurance verification transaction. In a related aspect, the point-of-sale device further includes a printer. In another aspect, the base unit further includes a display on the base unit housing and in communication with the processor. The base unit may also include a touch screen. In some aspects, the base unit further includes a keypad on the base unit housing and in communication with the processor. Relatedly, the base unit housing can further include a card slot for receiving a patient card. Similarly, the base unit can include a magnetic strip reader affixed with the base unit housing at the card slot and in communication with the processor. In a related aspect, the point-of-care device includes a modem located within the base unit housing and in communication with the processor. The point-of-sale device may also include an external communications interface in communication with the processor. In some aspects, the processor can receive and process Internet communications over the external communications interface.

In a second aspect, the present invention provides a point-of-care terminal for processing a healthcare transaction by a healthcare provider. The terminal can include a reader configured to read information from an information encoding region of a healthcare eligibility and settlement presentation instrument associated with a patient, and a processor configured to process a healthcare transaction based on the information. The healthcare transaction can include a healthcare eligibility verification transaction and/or a healthcare settlement transaction. In a related aspect, the healthcare transaction includes a healthcare eligibility transaction, and the processor is configured to transmit a healthcare eligibility request to a communication network and to receive a healthcare eligibility response from the communication network. Similarly, the healthcare transaction can include a healthcare settlement transaction that includes a credit card settlement, a debit card settlement, a flexible spending account settlement, a health savings account settlement, a health reimbursement account settlement, a medical savings account settlement, a transportation account settlement, a parking settlement, a dependent care settlement, and/or a claim settlement. In some aspects, the processor can be configured to transmit a request for an eligibility and coverage information packet to a communication network and to receive an eligibility and coverage information packet from the communication network. In a related aspect, the terminal further includes an external network interface, and the processor is configured to send the request and receive the packet via the external network interface.

In another aspect, the present invention provides a system for effectuating a healthcare transaction from one or more point-of-care devices. The system can include a plurality of point-of-care devices in communication with a point-of-care control system. At least one of the plurality of point-of-care devices can be in communication with a first transaction system and a second transaction system. In some aspects, each of the point-of-care control system, the first transaction system, and the second transaction system may be capable of configuring one or more of the plurality of point-of-care devices. In related aspects, the first transaction system is a healthcare eligibility verification system. In other related aspects, the second transaction system is a healthcare settlement system.

In yet another aspect, the present invention provides a computer program product for processing a healthcare transaction by a healthcare provider. The program product can include code for retrieving patient data from a healthcare presentation instrument, the healthcare presentation instrument associated with a patient, code for generating a request for a healthcare information packet based on the patient data from the healthcare presentation instrument, code for transmitting the request for a healthcare information packet to a communication network, code for receiving a healthcare information packet from the communication network, code for presenting at least part of the content of the healthcare information packet to the healthcare provider, and a computer-readable medium for storing the codes. In a related aspect, the healthcare presentation instrument includes a healthcare insurance eligibility and coverage instrument and the healthcare information packet includes a healthcare eligibility and coverage information packet. In some aspects, the computer program product also may include code for maintaining a record of healthcare information packet requests.

BRIEF DESCRIPTION OF THE DRAWINGS

FIG. 1A illustrates a system according to one embodiment of the present invention.

FIG. 1B illustrates a presentation instrument according to one embodiment of the present invention that may be used in conjunction with the system depicted in FIG. 1A.

FIGS. 3, 3A, 3B, and 3C illustrate healthcare transactions according to some embodiments of the present invention.

FIGS. 4, 4A, 4B, and 4C illustrate a healthcare transaction receipts according to some embodiments of the present invention.

FIGS. 5 and 6 illustrate healthcare transactions according to some embodiments of the present invention.

DETAILED DESCRIPTION OF THE INVENTION

Figure 1C:
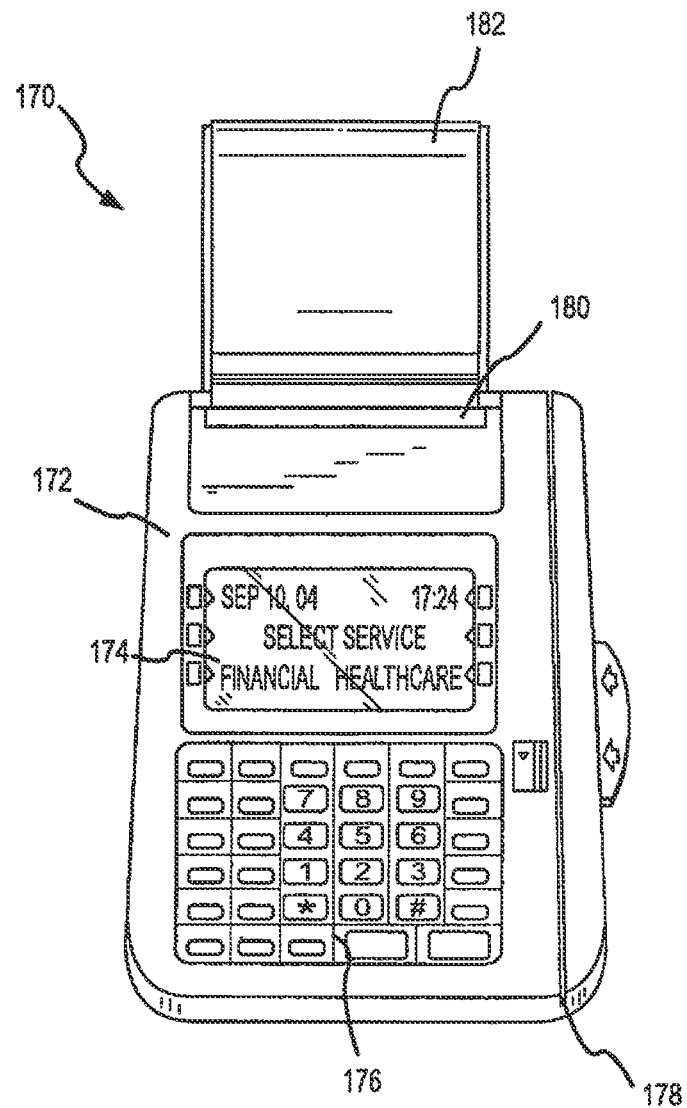
FIG. 1C illustrates a point-of-care terminal according to one embodiment of the present invention.

The present invention will find application in wide variety of healthcare settings. For example, by using a healthcare terminal device according to one embodiment of the present invention, a doctor can obtain insurance coverage information for a patient, process information for a claim adjudication, receive payment for services from a patient's credit card and/or FSA, obtain prescription information for the patient, and the like.

According to some embodiments of the invention, a health care provider (sometimes referred to herein simply as a "provider") starts the verification process of a patient's (also referred to herein as a "member") health insurance eligibility by reading information from a health insurance presentation instrument of the patient using a point-of-care device. Using this information, the provider sends a request for eligibility verification to a host computer system. Acting as an information clearing house, the host computer system consults stored information to determine to which of several payer (e.g., insurance company, third party administrator, self insured employer, or the like) systems the request should be forwarded. In response to the request from the host computer system, the appropriate payer system returns an eligibility and coverage information packet to the host computer system. The host computer system then forwards the packet to the provider via the point-of-care terminal that is deployed at the health care provider location. In some embodiments, the host computer system forwards the packet in a manner pre-selected by the provider. In other embodiments, the packet is forwarded in a manner identified in the request from the provider. Such manners include fax, email, Internet, IVR, healthcare terminal, Electronic Data Interchange (EDI), and the like.

Once care is provided, the same presentation instrument and point-of-care terminal may be used to settle payments due for the care. This may include the provider receiving payment from the payer or a third party administrator for covered services and/or from funds held in an FSA, HRA, and/or other balances of the patient. Further, a pharmacist may be reimbursed in similar fashion. If the patient owes a deductible or co-payment for covered services, the same presentation instrument may access a line of credit which the patient may use for such purposes. Of course, patients may settle accounts for visits to a dentist or other heath care-related provider in similar fashion. Thus, an employer may advantageously provide its employees the opportunity to access many different types of health care balances using a single presentation instrument.

Having described the present invention generally, attention is directed to FIG. 1A, which illustrates one exemplary embodiment of a system 100 according to the present invention. As will be explained in more detail hereinafter, the system 100 may be used to verify insurance coverage, process insurance claims, pay claims, obtain prescription information, and/or the like. It should be understood that while examples used herein may relate to medical insurance, this is not a requirement. Other types of insurance and prepaid services may benefit from the teachings herein, as is apparent to those skilled in the art in light of this disclosure.

The system 100 includes a host computer system 102, which in some cases may be referred to as a point of care control system. The host computer system 102 may include, for example, a server computer, a personal computer, a workstation, or other suitable computing device. The host computer system 102 includes application software that programs the host computer system 102 to perform one or more functions according to the present invention. For example, application software resident on the host computer system 102 may program the host computer system 102 to receive and process healthcare and/or financial transaction information such as patient insurance card and credit card transaction information. The host computer system 102 may include one or more of the aforementioned computing-devices, as well as storage devices such as databases, disk drives, optical drives, and the like. The host computer system 102 may be fully located within a single facility or distributed geographically, in which case a network may be used to integrate the host computer system 102. Many other examples are possible and apparent to those skilled in the art in light of this disclosure. Thus, this example of a system 100 according to the present invention is not to be considered limiting.

The system 100 also includes a first communication network 104. The first network 104 may be the Internet, an intranet, a wide area network (WAN), a local area network (LAN), a virtual private network, and combination of the foregoing, or the like. The network 104 may include both wired and wireless connections, including optical links. In some embodiments, the network 104 is a settlement network, such as a credit card transaction processing network. In some embodiments, eligibility may be verified at least partially through the first network. Through the network 104, provider devices 106 communicate with the host computer system 102.

The provider devices 106 include any devices capable of reading information from health insurance presentation instruments and transmitting the information through a communication link, such as the network 104, to a processing system, such as the host computer system 102. The information may be comprised by a referral, a request for eligibility verification, and/or a financial transaction settlement message. For example, the information may be a request by a doctor to an insurance company to confirm if a patient is eligible and covered by a payer for medical services requested. In some embodiments, the system will provide multi-payer connectivity, and including connectivity to governmental or other payer entities such as Medicaid or Medicare.

In some embodiments, network 104 or host computer system 102 may recognize a transaction as either a financial transaction or a healthcare transaction based on a specific message type. Terminal 106 may be configured to format information data in a request transaction, assign a message type, and transmit the request transaction to network 104 or other front-end platform. Network 104 may be configured to accept transactions from a variety of healthcare locations, including doctor's offices, hospitals, laboratories, and the like. Network 104 can then route transactions, such as eligibility requests, based upon data elements in the message type. In some embodiments, transactions identified as healthcare will be routed to host computer system 102 which may maintain continuous connectivity and processing with one or more payers 110 or clearinghouses to support the transaction process. In some embodiments, a payer 110 may be permitted a certain time limitation in which to process a request and return a response to host computer system 102. Payers 110 or other elements of the network may have specific rules or expectations based on 270/271 Electronic Data Interchange (EDI). When preparing a response, payers 110 may determine member status or eligibility based according to payer rules. In some cases the host computer system and/or the payer will maintain one or more databases of account numbers, which may be used to identify subscribers, providers, payers, locations, and the like. Host computer system 102 can route a request transaction to a payer 110 for a response. This request transaction can be routed to payer 110 either directly or through a clearinghouse. The response from payer 110 can be returned through network 104 to the POC terminal device 106. In some embodiments, an eligibility authorization will not guarantee coverage or payment of claims.

In some embodiments, provider devices 106 comprise a reader, such as a magnetic stripe reader, a smart chip reader, a bar code reader, or the like, in combination with a computing device. In some embodiments, the provider devices 106 comprise point-of-sale devices such as those more fully described in the previously-incorporated U.S. patent application Ser. Nos. 60/147,899, 09/634,901, 10/358,615, 10/116,686, 10/116,689, 10/116,891, and 10/116,735. In related embodiments, the provider devices 106 will support all existing transactions for standard point-of-sale devices for retail merchants (e.g. credit, debit, check, and the like) in addition to supporting healthcare specific transactions such as those described herein. In still other embodiments, the provider devices 106 comprise specially-designed computing and reading devices for reading information from a patient's insurance card, constructing a request for an eligibility and coverage information packet, and transmitting the request to the host computer system. In some embodiments, the provider devices 106 are capable of receiving eligibility and coverage information packets and displaying the information to a user. In other embodiments, the present invention includes a we-based system that can be accessed through a personal computer having a card-reader attachment. Those skilled in the art will recognize equivalent devices in light of this disclosure.

The provider devices 106 may be located at any of a wide variety of provider locations. By way of example and not limitation, these locations include doctor's offices, dentist's offices, pharmacies, hospitals, drug stores, chiropractor's offices, physical therapist's offices, and the like. Provider devices 106 also may communicate with the host computer system 102 through a second network 108. Devices 106 may be configured to support a password for healthcare and financial processing, which in some cases may be required or desired due to legislation, payer or provider rules, and the like. Password functionality can enhance a secure environment by preventing unauthorized access by personnel within the provider location.

The system 100 may also include a second network 108, which may include any of the aforementioned networks. The first network 104 and the second network 108 may be the same network, different networks, or portions of a larger network. The second network 108 provides a connection between the host computer system 102 and payer computing systems 110, among other things. In some instances, one network can include a healthcare eligibility verification system, and separate network can include a healthcare financial settlement system. In related embodiments, a single network can include both a healthcare eligibility verification system and a healthcare financial settlement system.

The payer computing systems 110 may be any computing system that provides access to data. Associated storage devices may include solid state memory, such as RAM, ROM, PROM, and the like, magnetic memory, such as disc drives, tape storage, and the like, and/or optical memory, such as DVD. The payer computing systems 110 may be co-located with the host computer system 102, may be integral with the host computer system 102, or may be located apart from the host computer system 102.

The system 100 also may include member computing systems 112 and third party administrator computing systems 114, each of which may be any of the aforementioned computing system types. Members may view information relating to their benefits by accessing the host computing system 102, while payers (e.g., insurance company, third party administrator, self insured employer, or the like) may send and receive information necessary to process claims and settle FSA, HSA and other healthcare and stored value balances on behalf of payers and members. In addition to providing host computing system 102, hosts can also also provide customer service, reporting, archival, switching, terminal or PC applications or solutions, payer interfaces, patient cards, an Automated Clearing House (ACH), Electronic Remittance Advice (ERA), Electronic Funds Transfer (EFT), multipurpose accounts with multiple funds, and other products or services for use with provider device 106.

In some embodiments, the system 100 also includes a specialty network 116, which, in a specific embodiment is a pharmacy network. The specialty network may be any of the aforementioned network types. Through the specialty network 116, certain providers 106 (e.g., pharmacists, drug stores, cash register system providers, and the like) may interact with the host computer system to settle claims for certain covered items such as prescription drugs and IRS approved OTC items. In some embodiments, a specialty services administrator 118 (e.g., a pharmacy benefits administrator, cash register system provider) is also tied into this network and involved in the process.

In related embodiments, system 100 can be configured to transfer healthcare claim adjudication requests and responses to various components of the system. Such requests and responses may include a list of individual services and a compilation of complete eligibility information. Typically, a claim request will be routed to a payer which may perform real-time adjudication or re-pricing. A payer can generate a response including claim adjudication information and re-pricing amounts. Often, a transaction will include a payer generated Explanation of Benefits (EOB), which may be provided to a patient at the time of service. In some cases, the system may effect a transaction, such as a fund credit, with a Healthcare Spending Account (HSA), a Flexible Spending Account (FSA), or a Health Reimbursement Arrangement (HRA) account. The system may also provide the patient with a receipt of payment at the time of service, and this receipt may be generated by a provider. A payer generated response may also be interfaced with a Practice Management System (PMS). Systems according to the present invention enable a payer to automatically adjudicate claims, update claims records, update provider reconciliation accounts, send payment for all services, and in some instances may reduce the number of EOB's for services provided. Systems may also enable providers to automatically update patients records, to settle credit card balances, update claims records, update payer reconciliation accounts, and receive payment for all services, regardless of payment fund or source. Systems may find use in laboratories, hospitals, and large group practices. In some instances, systems will provide for batch transmission of transactions such as eligibility transactions.

FIG. 1B illustrates an embodiment of a health care presentation instrument 150 according to an embodiment of the invention. Presentation instrument 150 can be used to identify the member (i.e., patient, employee, or covered individual) to providers, and provide information to the provider device 106 used to verify eligibility and/or settle claims. In one embodiment, the presentation instrument 150 comprises what consumers commonly recognize as a credit card or debit card. One side of the card is embossed with the member's name 152, an account number 154, an expiration date 156, and the like. The card may have a logo 158 of the payer. Additionally, the card may have other recognizable features that identify it as a branded credit card. In some embodiments, the instrument may be a health care eligibility and settlement or payment presentation instrument.

The back side of the card may include a signature line 160 and plan information 162. Plan information 162 may include a group number, a plan administrator phone number, and other similar information. In some embodiments, information such as deductibles, co-payments, specific pharmacy data, and the like is included. In other embodiments, this type information is intentionally omitted to improve flexibility by allowing such information to be changed without necessitating card reissuance. In some embodiments, the card may support swipe-less functionality whereby information can be read from the card by waving it in front of or near a reader configured for this purpose. Such a reader can be integral to or otherwise connected with the terminal. Such an approach may employ RFID technology.

The card also includes one or more information encoding features. Information encoding features may include a magnetic stripe 164, a bar code 166, a smart chip (not shown), and the like. It is to be understood that many other examples of a healthcare presentation instrument and associated information encoding features are possible. In some embodiments, a card may include a magnetic stripe configuration having attributes in three tracks. Tracks 1 and 2 can contain MASTERCARD/VISA requirements, and Track 3 can be configured to support healthcare applications such as eligibility functionality. In some embodiments, Track 2 may include an account number having an ISO prefix to identify a payer. In some embodiments, Track 3 may include a subscriber identification number. Similarly, it is appreciated that any of the Tracks may be configured to support healthcare applications such as eligibility and settlement functionality.

Table 1 provides a Track 3 configuration for a presentation instrument according to one embodiment of the present invention.

TABLE 1

Track 3 configuration (Alpha/Numeric, 107 characters)

| Field Type | Field Name | Field No. | Field Length | Character |
| --- | --- | --- | --- | --- |
| Common | Start Sentinel | 1 | 1 | _; (underscore and semicolon) |
| Common | Format Code | 2 | 1 | |
| Common | Payer ID | 3 | 6 | |
| Common | Separator | 4 | 1 | = |
| Common | Subscriber ID | 5 | 20 (includes 2 positions for member sequence if required) | |
| Common | Separator | 6 | 1 | |
| Common | Subscriber DOB | 7 | 8 (DD/MM/CCYY) | |
| Common | Separator | 8 | 1 | = |
| Common | Subscriber Name | 9 | 26-optional field | |
| Common | Separator | 10 | 1 | = |
| Distinctive | Group/Policy# | 11 | 15-optional field | |
| Common | End Sentinel | last | 1 | ? |

FIG. 1C illustrates a mechanical layout of provider device or point-of-care (POC) terminal 170 in accordance with one embodiment of the present invention. POC device 170 can be positioned horizontally, such as on a counter, or it may be mounted on a wall. In some embodiments, terminal 170 is capable of supporting an external keyboard or other input device or means that is not integral with the terminal POS device 170 typically includes a housing 172 for containing certain internal components. Further, POC device 170 can include a display 174 and a keypad 176 that may be used for the display and entry of data, respectively. Display 174 may be monochromatic, although in alternative embodiments a color display is provided. Keypad 176 is illustrated as having thirty-five keys, although another number of keys as suitable for specific applications may be used. A magnetic-stripe reader 178, which in one embodiment is bi-directional, is also provided on POC device 170 for reading magnetic-stripes that may be included, for example, on a health insurance presentation instrument or a credit or debit card. POC terminal may also include a printer 180 and a paper roll 182. It is understood that a POC device 170 according to the present invention may include any element, configuration, or functionality of a point-of-service (POS) device as described in the previously-incorporated U.S. patent application Ser. Nos. 60/147,899, 09/634,901, 10/358,615, 10/116,686, 10/116,689, 10/116,891, and 10/116,735. Further, POC terminal 170 can be configured to include or interface with PC products or web solutions that process credit card and/or debit card financial transactions in order to support any of the financial and healthcare operations contemplated by this application. For example, software and hardware components of device terminal 170 may be connected or interfaced with ICVERIFY, WEBAUTHORIZE, YOURPAY.COM, and the like. In some instances, web solutions, including IP solutions, provide for quick transactions such that high transaction volumes can be accommodated. The illustrated embodiments described herein show combinations of different features that may be included in specific embodiments, although it will be appreciated that additional embodiments will derive from further combinations of features, and perhaps also the addition or absence of certain features.

Figure 2:
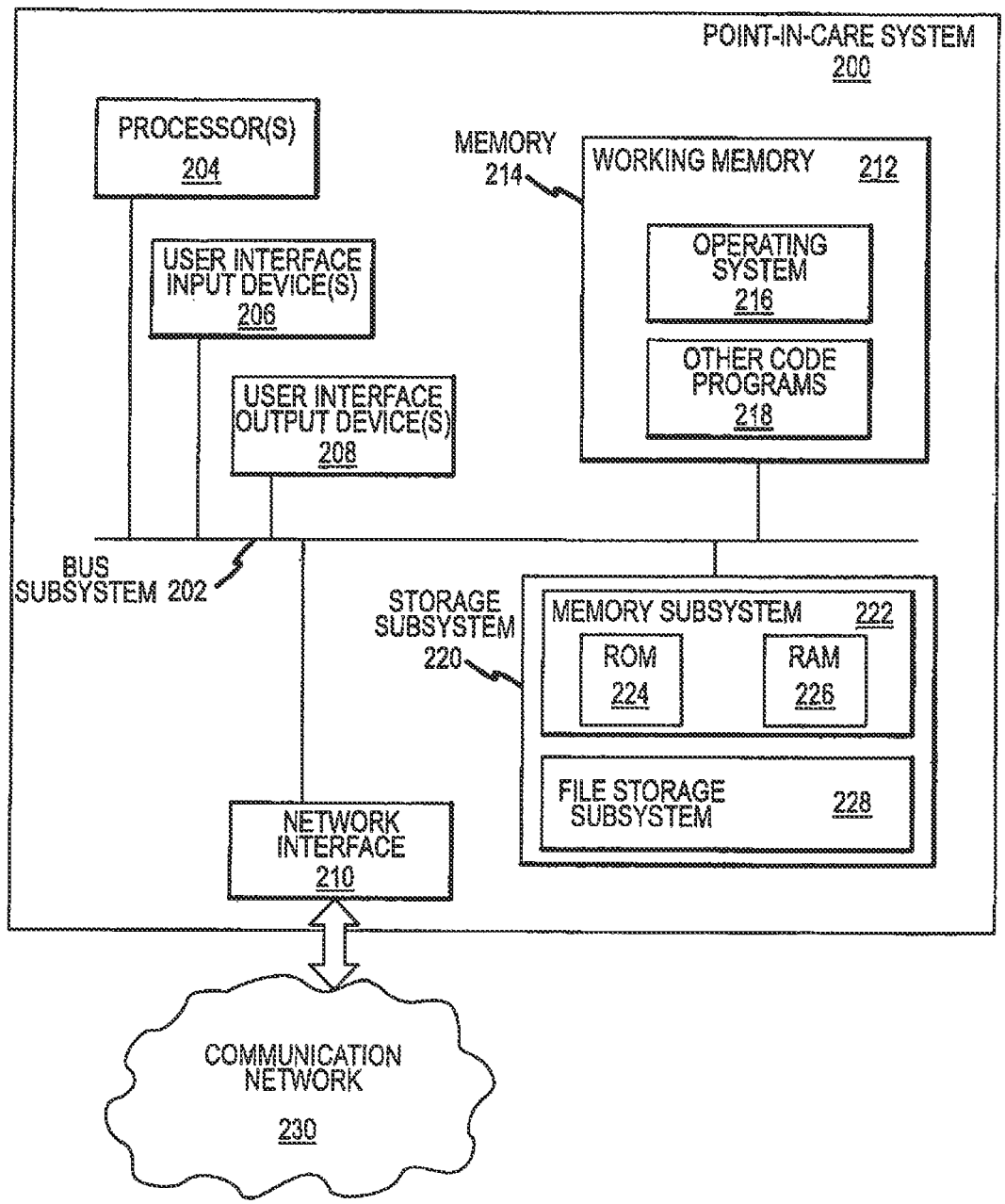
FIG. 2 illustrates a simplified computer system according to an embodiment of the present invention.

FIG. 2 is a simplified block diagram of an exemplary computer system that broadly illustrates how individual system elements for a POC system 200 may be implemented in a separated or more integrated manner. POC system 200 is shown comprised of hardware elements that are electrically coupled via a bus subsystem 202, including one or more processors 204, one or more input devices 206 such as user interface input devices, one or more output devices 208 such as user interface output devices, and a network interface 210.

In some embodiments POC system 200 also comprises software elements, shown as being currently located within working memory 212 of memory 214, including an operating system 216 and other code 218, such as a program designed to implement methods of the invention.

Likewise, in some embodiments POC system 200 may also include a storage subsystem 220 that can store the basic programming and data constructs that provide the functionality of the various embodiments of the present invention. For example, software modules implementing the functionality of the methods of the present invention, as described herein, may be stored in storage subsystem 220. These software modules are generally executed by the one or more processors 204. In a distributed environment, the software modules may be stored on a plurality of computer systems and executed by processors of the plurality of computer systems. Storage subsystem 220 can include memory subsystem 222 and file storage subsystem 228. Memory subsystem 222 may include a number of memories including a main random access memory (RAM) 226 for storage of instructions and data during program execution and a read only memory (ROM) 224 in which fixed instructions are stored. File storage subsystem 228 can provide persistent (non-volatile) storage for program and data files, and may include tangible storage media which may optionally embody patient, provider, payer, or other healthcare or financial data. File storage subsystem 228 may include a hard disk drive, a floppy disk drive along with associated removable media, a Compact Digital Read Only Memory (CD-ROM) drive, an optical drive, DVD, CD-R, CD-RW, solid-state removable memory, other removable media cartridges or disks, and the like. One or more of the drives may be located at remote locations on other connected computers at other sites coupled to POC system 200. The modules implementing the functionality of the present invention may be stored by file storage subsystem 228. In some embodiments, the software or code will provide protocol to allow the POC system 200 to communicate with communication network 230. Often such communications will include dial-up or internet connection communications.

It is appreciated that system 200 can be configured to carry out various methods of the present invention. For example, processor component or module 204 can be a microprocessor control module configured to receive healthcare transaction signals from input device or module 206, and transmit healthcare transaction signals to output device or module 208 and/or network interface device or module 210. Each of the devices or modules of the present invention can include software modules on a computer readable medium that is processed by a processor, hardware modules, or any combination thereof. Any of a variety of commonly used platforms, such as Windows, MacIntosh, and Unix, along with any of a variety of commonly used programming languages, may be used to implement the present invention.

User interface input devices 206 may include, for example, a touchpad, a keyboard, pointing devices such as a mouse, a trackball, a graphics tablet, a scanner, a joystick, a touchscreen incorporated into a display, audio input devices such as voice recognition systems, microphones, and other types of input devices. User input devices 206 may also download a computer executable code from a tangible storage media or from communication network 230, the code embodying any of the methods of the present invention. It will be appreciated that terminal software may be updated from time to time and downloaded to the terminal as appropriate. In general, use of the term "input device" is intended to include a variety of conventional and proprietary devices and ways to input information into POC system 200.

User interface output devices 206 may include, for example, a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 200 to a user.

Bus subsystem 202 provides a mechanism for letting the various components and subsystems of POC system 200 communicate with each other as intended. The various subsystems and components of POC system 200 need not be at the same physical location but may be distributed at various locations within a distributed network. Although bus subsystem 202 is shown schematically as a single bus, alternate embodiments of the bus subsystem may utilize multiple busses.

Network interface 210 can provide an interface to an outside network 230 and/or other devices. Outside communication network 230 can be configured to effect communications as needed with providers and payers. It thus receives an electronic packet from POS system 200 and transmits any eligibility or payment authorizations as needed back to POS system 200. In addition to providing such infrastructure communications links internal to the system, the communications network system 230 may also provide a connection to other networks such as the internet and may comprise a wired, wireless, modem, and/or other type of interfacing connection.

It will be apparent to those skilled in the art that substantial variations may be used in accordance with specific requirements. For example, customized hardware might also be used and/or particular elements might be implemented in hardware, software (including portable software, such as applets), or both. Further, connection to other computing devices such as network input/output devices may be employed. POC terminal system 200 itself can be of varying types including a computer terminal, a personal computer, a portable computer, a workstation, a network computer, or any other data processing system. Due to the ever-changing nature of computers and networks, the description of POC system 200 depicted in FIG. 2 is intended only as a specific example for purposes of illustrating one embodiment of the present invention. Many other configurations of POC system 200 are possible having more or less components than the computer system depicted in FIG. 2. Relatedly, any of the hardware and software components discussed above can be integrated with or configured to interface with other practice management systems used at provider locations.

In some embodiments, the POC system 200 can be configured to accept a request and to recognize the request as a healthcare request, a credit request, a debit request, a check request, and the like. Relatedly, the POC system may be configured to support financial functionality for retail activity (e.g. credit, debit, and check), merchant setup/edit, and parameter downloads, as well as for related functionality for healthcare applications. In some embodiments, POC system 200 will be configured to accept healthcare input data from an operator, format the healthcare data into a request transaction, assign a healthcare header/trailer record to the request transaction, and transmit the request transaction to communication network 230. It will be appreciated that POC system 200 may be used at any of a variety of locations, including doctor's office, hospitals, labs, and the like, and that communication network 230 can be configured to accept transactions from any of these locations. POC system 200 will often be configured to send provider-specific information along with any healthcare transaction. This information can be part of data elements that are downloaded into the terminal Relatedly, POC system 200 may include software to support various healthcare related fields that may need to be updated and/or edited via download or manually. Such situations may occur, for example, when it is necessary to change a doctor's name or to change a provider number.

In one embodiment, POC system 200 will include a HYPERCOM T7PLUS terminal as commercialized by HYPERCOM CORPORATION. System 200 may include a 128×64 graphic display, adapted for displaying 8 lines of 20 characters; 35 standard keys plus 6 ATM style screen keys; 2 megabytes of memory; an integrated printer with 3" paper supporting up to 64 characters per line with same font used with 2" paper; an integrated smart card reader; a 56K modem; and an integrated Track I, II, and III card reader. System 200 may also be PIN enabled or configured to operate in association with an external PIN pad to provide PIN functionality. In some embodiments, POC terminal 200 can be configured to interface with an external printer such as a standard PC-driven type printer.

System 200 may be provided with any of a variety of singular or combination application configurations to support, for example, healthcare eligibility and financial transactions submitted by a provider. In some embodiments, an application configuration can employ software and/or hardware functionality for healthcare activity only, or for healthcare and financial activity (e.g., credit, debit, or check) combined. System 200 can be adapted to receive automated parameter downloads and automated program downloads from, for example, communication network 230. In some embodiments, these downloads may be password-protected. In some embodiments, application software can run on a HYPERCOM T7PLUS 2 MB terminal, wide paper printer model. Terminal system 200 may be configured for both financial and healthcare transactions, or for healthcare transactions only. It will be appreciated that the terminal itself may carry out certain operations required for these transactions, and that the terminal may interface with other computers or systems that carry out some certain operations required for these transactions.

Terminal system 200 can be configured to effect any of a variety of healthcare or financial transactions. A healthcare eligibility request transaction, for example, can be a request from a provider (e.g. doctor) to a payer (e.g. insurance company) to confirm that a patient (e.g. subscriber or dependent) is covered by the payer for the medical services requested. Such a transaction can be submitted as a real-time Electronic Data Interchange (EDI) that is compliant with certain governmental regulations such as The Health Insurance Portability and Accountability Act of 1996 (HIPAA). The terminal can use various applications to recognize and send healthcare or other data to other system networks, which may then format the data into HIPAA compliant format, and forward the data to another communication portal such as a clearinghouse or a direct connection to the payer. The data may also be returned to the terminal as a readable output message. Formatting may also be accomplished at least in part by the terminal. Any of a variety of healthcare claim formats or transactions may be supported by the instant invention, including claim transactions, claims payment transactions, real-time claim adjudications, line item adjudicated results, claim inquiries, referral/pre-certifications, amount of patient responsibility, and the like. Transactions can include various parameters including amount paid to provider, total of all line items, adjudication amount, paid amount, patient responsibility (e.g., co-pay, deductible), balance, payment, patient card data, fund balance, electronic funds transfer, auto or patient select, various attributes of fund balance, and the like. The present invention may also support or include an interface with a Practice Management System (PMS).

It is recognized that systems according to the present invention may be configured to the needs of a particular provider. For example, some systems can provide for the ability to include Procedure or Service-Type codes within an eligibility request, and can provide database functionality for storing and/or maintaining such codes. These codes may be implemented by, defined by, or otherwise configured for a provider, and may include codes specific for the provider's practice. Table 2 provides an exemplary menu of provider-defined pre-selected codes for an OB-GYN healthcare provider.

TABLE 2

| Service Code No. | Service Code Description |
| --- | --- |
| 1 | Medical Care |
| 3 | Consultation |
| 30 | Health Benefit Plan Coverage (default value for all Phase 1 transactions) |
| 65 | Newborn Care |
| 68 | Well Baby Care |
| 69 | Maternity |
| 81 | Routine Physical |
| 82 | Family Planning |
| 83 | Infertility |
| 84 | Abortion |
| BE | Massage Therapy |
| BH | Pediatric |

A point-of-care terminal can be configured to present codes such as these Service Type codes to a provider during a healthcare transaction. Relatedly, the terminal may be configured to accommodate a variable length 271 response for each individual Service Type code. A response may include a minimum of one Service Type code and a maximum of 'x' Service Type codes.

FIG. 3 depicts a Healthcare Eligibility transaction 300 according to one embodiment of the present invention. The left column represents provider operations to be input into the system, for example via a touchpad of POC terminal. The right column represents instructions or other communications presented to the provider, for example, on a display screen of POC terminal. It will be appreciated that POC system may or may not require answers to each of the prompts discussed below. If a field is not required, the system may allow the user to continue to the next prompt.

In an idle state, the system presents a Root prompt 304 to the provider or user. Alternatively, a provider can initiate a Healthcare Eligibility transaction by pressing a "CANCEL" key on the touchpad, as shown in step 302 when the system is not in the Root prompt mode, in order to present a Root prompt 304 to the provider. In some embodiments, access to or operation of the terminal may require a user-input password. Root prompt 304 includes a date and time stamp display, and a transaction Select Service that contains Financial and Healthcare transaction options. Presented with Root output 304, provider selects the Healthcare transaction option by pressing a "HEALTHCARE" key on the touchpad, step 306. System then presents a Select Service prompt 308 to the provider. Select Service prompt 308 includes Eligibility, Report, and Reset options. In this example, provider chooses the Eligibility service by pressing an "ELIGIBILITY" key on the touchpad, step 310. System then presents a Patient Card/Payer ID prompt 312 to the provider, prompt 312 containing instructions to either swipe a patient card or enter a payer identification number. Provider can continue by either swiping a patient card or entering a payer identification number and pressing an "ENTER" key on the touchpad, as shown in step 314.

System then presents a Provider prompt 316 to the provider. Provider prompt 316 invites the provider to key in a provider identification number, which provider may complete by keying in the number and pressing the "ENTER" key on the touchpad, step 318. Thereafter, system presents a Patient Type Selection prompt 320 to the provider, the Patient Type Selection prompt 320 containing instructions for the provider to select the patient type, for example the patient herself, the patient's child, the patient's spouse, or other patient type. Provider can then select the appropriate Patient Type option by pressing the corresponding key on the touchpad, as indicated at step 322. System then presents a Patient Date of Birth prompt 324 to the provider, in response to which the provider may key in the patient's date of birth (e.g. in MMDDYYYY format) and press the "ENTER" key on the touchpad, as depicted in step 326. System 200 then presents a Date of Service prompt 328 to the provider, in response to which the provider may key in the date of service (e.g. in MMDDYYYY format) and press the "ENTER" key on the touchpad, as depicted in step 330. Alternatively, the provider may simply press "ENTER" to default to Today's Date. System then presents a Policy/Group Number prompt 332 to the provider, in response to which the provider may key in the Policy/Group Number and press the "ENTER" key on the touchpad, as depicted in step 334.

System then presents a Subscriber Identification Number prompt 336 to the provider. Subscriber Identification Number prompt 336 invites the provider to key in a subscriber identification number, which provider may complete by keying in the number and pressing the "ENTER" key on the touchpad, step 338. In some embodiments the subscriber identification number and/or other subscriber or patient information can be read directly from a presentation instrument, for example from a magnetic stripe of a benefit card that is swiped in the terminal, and therefore does not need to be manually input into the terminal. In related cases, such functionality may be limited to those presentation instruments that are configured to meet certain specifications. System then presents a First Name prompt 340 to the provider, in response to which the provider may key in the subscriber's first name and press the "ENTER" key on the touchpad, as depicted in step 342. Subsequently, system presents a Last Name prompt 344 to the provider, in response to which the provider may key in the subscriber's last name and press the "ENTER" key on the touchpad, as depicted in step 346. As depicted in FIG. 2, system can then communicate with a host (e.g. communication network 230) to complete the Healthcare Eligibility transaction. This step may be initiated by the provider pressing the "ENTER" key on touchpad after entering the Subscriber Last Name. System can indicate a communication status by presenting a Host Communication signal 348 to the provider. System can send the request to a host system which then sends the request to a payer or clearinghouse, as shown in FIG. 1A.

Further, system can print a receipt, such as a Healthcare Eligibility Receipt. During the printing process, the system may indicate a printing status by presenting a Printing signal 350 to the provider. Subsequent to printing a first Eligibility Receipt, system can present a Reprint prompt 352 to the provider, in response to which the provider can select the desired response by pressing a "NO" or "YES" key on the touchpad as indicated at step 354. If "YES' is selected, System can again present Reprint prompt 352 to the provider, allowing the provider to optionally print several receipts. When the desired number of receipts have been printed, provider may terminate the eligibility transaction by twice pressing the "CANCEL" key on the touchpad (if "YES" was selected) or by once pressing the 'CANCEL" key (if 'NO" was selected), as indicated at step 356. Thereafter, system presents an idle prompt 358 to provider, and stands ready to process another transaction. In some cases, the terminal will time-out if there is no activity for a certain amount of time (e.g. 20 seconds) and return to the Root prompt.

In some cases, payers may or may not be supported on a specific network or clearinghouse. If a payer is not found to be supported, the system may be configured to return a message to the operator indicating that the payer is not found and suggesting that the operator call or otherwise contact the payer or use a payer specific web-site for authorization. In a related embodiment, the receipt may indicate that the payer that is provided to the terminal is not currently supported by the system, and recommend that the provider verify and re-enter the payer information. In some embodiments, a patient card will contain a 16 digit account number in ISO (International Organization for Standardization) format, which may be on Track 2 of the card. Track 2 may include an account number having an ISO prefix to identify a payer. In some embodiments, Track 3 may include a subscriber identification number. POC terminal may be configured to verify the account number against an internal or external healthcare prefix table which contains ISO prefixes for those payers which are associated with a specified network. It is understood that such tables may be updated periodically according to payer membership. In some embodiments, the prefix table includes a prefix field and a payer name field. Based upon the verification between the account number and the prefix table, various prompting sequences may be initiated. In some embodiments, the substance of the prompting sequence is based on whether the payer is associated with the specified network or whether the patient presents a card.

For example, FIG. 3A illustrates a healthcare transaction 300a wherein a payer is within the desired network. As noted above, in an idle state, the system can present a Root prompt 304a to the provider or user. Alternatively, a provider can initiate a Healthcare Eligibility transaction by pressing a "CANCEL" key on the touchpad, as shown in step 302a when the system is not in the Root prompt mode, in order to present a Root prompt 304a to the provider. In some embodiments, access to or operation of the terminal may require a user-input password. If the payer is in the specified network, in response to a card swipe or keyed Payer ID as shown at step 314a, POC system may verify a subscriber identification number and subscriber date of birth which are on Track 3 of the card. System then presents a Provider ID or Menu prompt 316a to the provider. Provider ID or Menu prompt invites the provider to key in a provider identification number and press the "ENTER" key or to press the "MENU" key, as depicted at step 318a. If the provider selects "MENU," system then presents a Provider Table prompt 320a to the provider. Provider Table prompt 320a invites the provider to key in a provider number, which provider may complete by keying in the number and pressing the "ENTER" key on the touchpad, step 322a. Alternatively, provider may select the provider name at step 322a. System then presents a Patient Type prompt 324a to the provider, in response to which the provider may key in the desired option, step 326a. System can then process the transaction as described elsewhere herein.

In some embodiments, if a payer is not within a desired network, the terminal may prompt the provider as if a card is not presented, as described below in relation to FIG. 3C. Relatedly, FIG. 3B illustrates another embodiment of a healthcare transaction 300b wherein a payer is not within the desired network. In response to a card swipe or a provider pressing the "MENU" key as shown at step 314b, POC system can present a Payer List or Table prompt 316b to the provider. Payer List or Table prompt invites the provider to key in a payer identification number and press the "ENTER" key, or selecting a payer name, as depicted at step 318b. System then presents a Provider ID or Menu prompt 320b to the provider. Provider ID or Menu prompt invites the provider to key in a provider identification number and press the "ENTER" key or to press the "MENU" key, as depicted at step 322b. If the provider selects "MENU," system then presents a Provider Table prompt 324b to the provider. Provider Table prompt 324b invites the provider to key in a provider number, which provider may complete by keying in the number and pressing the "ENTER" key on the touchpad, or by selecting a provider name, as shown in step 326b. System then presents a Policy/Group Number prompt 328b to the provider, in response to which the provider may key in the Policy/Group Number and press the "ENTER" key on the touchpad, as depicted in step 330b. System then presents a Subscriber Identification Number prompt 332b to the provider. Subscriber Identification Number prompt 332b invites the provider to key in a subscriber identification number, which provider may complete by keying in the number and pressing the "ENTER" key on the touchpad, step 334b. System can then process the transaction as described elsewhere herein.

FIG. 3C illustrates a healthcare transaction 300c wherein a card is not presented to a provider. Provider can call or otherwise contact the payer for authorization. Optionally, the provider may either select "Other" and key the payer identification number or select the payer by name and press the "ENTER" key System then presents a Provider ID or Menu prompt 320c to the provider. Provider ID or Menu prompt invites the provider to key in a provider identification number or select provider name and press the "ENTER" key. System then presents a Policy/Group Number prompt 328c to the provider, in response to which the provider may key in the Policy/Group Number and press the "ENTER" key on the touchpad, as depicted in step 330c. System then presents a Subscriber Identification Number prompt 332c to the provider. Subscriber Identification Number prompt 332c invites the provider to key in a subscriber identification number, which provider may complete by keying in the number and pressing the "ENTER" key on the touchpad, step 334c.

System can then process the transaction as described herein. With regard to the Date of Service prompts discussed above, the terminal may be configured to default to the actual date of the transaction, or to a date that is prior to or subsequent to that date.

Figure 4:
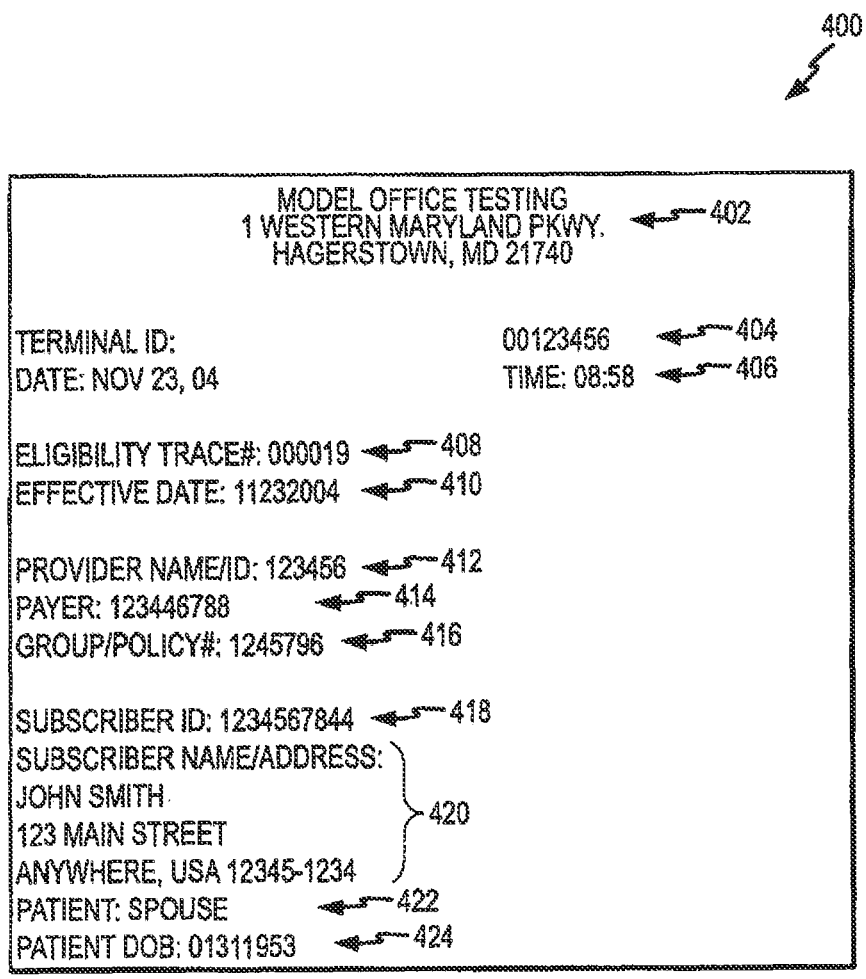

FIG. 4 depicts a Healthcare Eligibility Receipt 400 as generated by terminal system according to one embodiment of the present invention. Such receipts will often contain all data that is passed from the payer to the provider, and may be contained as part of a 271 EDI message format. For example, receipts can include the date of provided service, effective date of coverage, member number, group number, group name, CoPay amount, and Procedure/Category Codes with approval/decline indicator. The message length returning to the POC may be lengthy depending on the requirements of the individual payer. As shown in FIG. 4, an exemplary Healthcare Eligibility Receipt 400 can include a provider name and address field 402, a terminal identification number field 404, a date and time stamp field 406, an eligibility trace number field 408, an effective date field 410, a provider name and/or identification number field 412, a payer field, 414, a group/policy number field 416, a subscriber identification number field 418, a subscriber name/address field 420, a patient field 422, and a patient date-of-birth field 424. It is understood that terminal system can be configured to generate any of a variety of healthcare and financial receipts or other outputs. FIG. 4A depicts an example of an accepted eligibility receipt 400a. FIG. 4B illustrates an example of an accepted eligibility receipt with co-pay information from the payer 400b. FIG. 4C depicts an example of a rejected eligibility receipt 400c.

In addition to the eligibility transaction discussed above, POC system may be configured to process other types of healthcare and financial transactions. In some embodiments, system may retain data for each healthcare transaction until the credit batch is closed or until the healthcare batch is manually cleared. FIG. 5 illustrates a Reset Healthcare Batch transaction 500 according to one embodiment of the present invention. The "reset" function can allow the user to direct the application to zero-out all counts and start over. A provider can initiate a Reset Healthcare Batch transaction by pressing a "CANCEL" key on the touchpad, as shown in step 502. In response, system presents a Root prompt 504 to the provider. Root prompt 504 includes a date and time stamp field 504a, and a transaction selection field 504b that contains Financial and Healthcare transaction options. Presented with Root output 504, provider selects the Healthcare transaction option by pressing a "HEALTHCARE" key on the touchpad, step 506. System then presents a Select Service prompt 508 to the provider. Select Service prompt 508 includes Eligibility, Report, and Reset options. In this example, provider chooses the Reset service by pressing an "RESET" key on the touchpad, step 510. System then presents a Print prompt 512 to the provider, prompt 512 inviting provider to either print eligibility totals. The Report function can allow the user to print out an activity report which shows eligibility activity categorized by provider, payer, and the like. Provider can select the desired response by pressing a "NO" or "YES" key on the touchpad as indicated at step 514. During the printing process, the system may indicate a printing status by presenting a Printing signal 516 to the provider. Subsequent to printing a first Batch Report, system can again present Print prompt 512 to the provider, allowing the provider to optionally print several reports. When the desired number of reports have been printed, provider may terminate the eligibility transaction by pressing the "CANCEL" key on the touchpad, as indicated at step 518. Thereafter, system presents an idle prompt 520 to provider, and stands ready to process another transaction. In some embodiments, system may be configured such that the Healthcare Batch can not be reset separately from the financial batch. In such embodiments, it may be necessary for the provider to settle the financial batch prior to completing the reset function of the Healthcare Batch.

FIG. 6 illustrates a Healthcare Report transaction 600 according to one embodiment of the present invention. A provider can initiate a Healthcare Report transaction by pressing a "HEALTHCARE" key on the touchpad, step 606. System then presents a Select Service prompt 608 to the provider. Select Service prompt 608 includes Eligibility, Report, and Reset options. In this example, provider chooses the Report service by pressing an "REPORT" key on the touchpad, step 610. During the printing process, the system may indicate a printing status by presenting a Printing signal 612 to the provider. Subsequent to printing a Healthcare Report, system can again present Root prompt 604, and stands ready to process another transaction.

Figure 7:
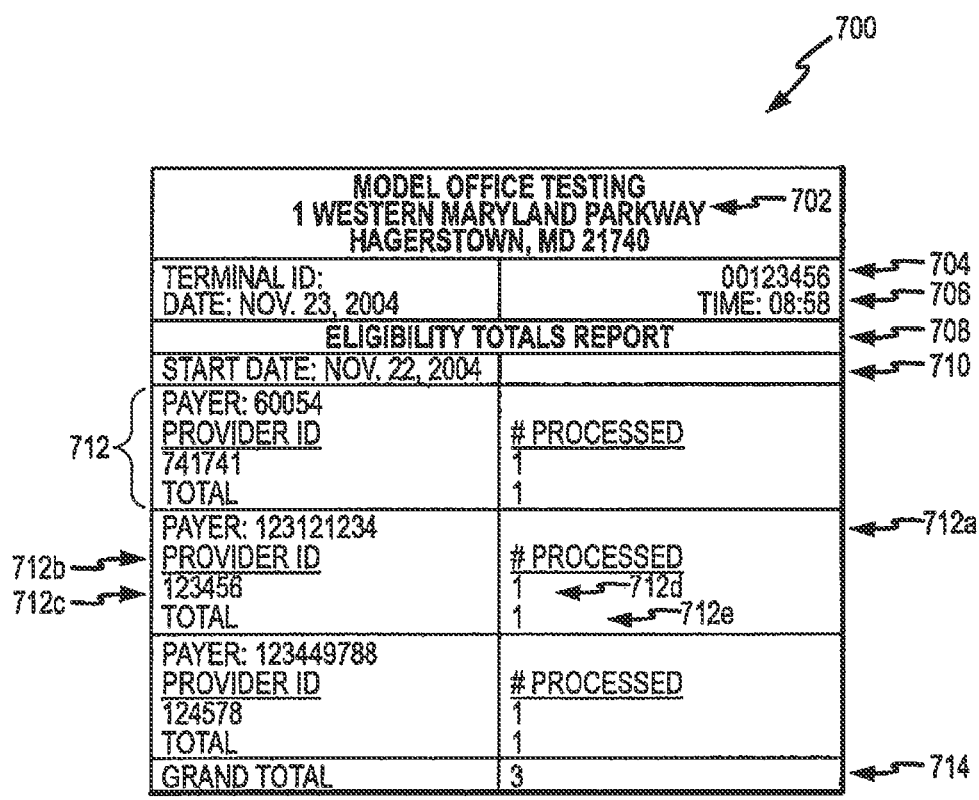
FIG. 7 illustrates a healthcare transaction report according to one embodiment of the present invention.

FIG. 7 depicts a Healthcare Report 700, or batch report, as generated by POC terminal system according to one embodiment of the present invention. Healthcare Report 700 can include a provider name and address field 702, a terminal identification number field 704, a date and time stamp field 706, an Eligibility Totals Report title line 708, a start date field 710, and one or more eligibility transaction summaries 712. Each eligibility transaction summary may include, for example, a payer number 712a, and a provider table 712b which contains a list of provider identification numbers 712c, the corresponding number of eligibility transactions or requests 712d processed at that provider, and the total number of transactions 712e processed in association with that payer number 712a. Healthcare Report 700 also can include a grand total 714 of all eligibility transactions processed during the time period between the date 706 and the start date 710. A single report may contain data for multiple providers. A terminal report can be generated by all providers who use the terminal. In some embodiments, the terminal can automatically reset all totals to zero upon execution of the batch report.

In the foregoing specification, the invention has been described with reference to specific exemplary embodiments thereof. It will be evident that various modifications and changes may be made thereunto without departing from the broader spirit and scope of the invention as set forth in the appended claims. It can be appreciated by one of skill in the art that all parameters, variables, factors, and the like can be incorporated into method steps or system modules, and similarly, that any method step can be effected by a system module including a software module, a hardware module, or a combination thereof. Further, various programming languages and techniques can be used to implement the disclosed invention. In addition, the specific logic presented to accomplish tasks within the present invention may be modified without departing from the scope of the invention. Many such changes or modifications will be readily apparent to one of ordinary skill in the art. The specification and drawings are, accordingly, to be regarded in an illustrative rather than a restrictive sense, the invention being limited only by the provided claims.

What is claimed is:

1. A point-of-care device, comprising:
a display;
a presentation instrument reader that reads a healthcare subscriber identifier and a financial account identifier from a presentation instrument;
one or more processors; and
a memory communicatively coupled with and readable by the one or more processors and having stored therein processor-readable instructions which, when executed by the one or more processors, cause the one or more processors to:
present, via the display, a menu allowing selection from multiple types of transactions, the multiple types of transactions comprising: a financial transaction and a healthcare eligibility transaction;
present, via the display, a first option associated with the financial transaction and a second option associated with the healthcare eligibility transaction, wherein the first option and second option are presented simultaneously;
receive a first selection of the healthcare eligibility transaction from the multiple types of transactions presented as part of the menu;
receive the healthcare subscriber identifier associated with a patient via the presentation instrument reader;
transmit a first message comprising the healthcare subscriber identifier via a settlement network to a host system initiating the healthcare eligibility transaction;
receive, in response to the first message, via the settlement network from the host system, an accepted eligibility receipt that indicates a co-pay amount corresponding to a healthcare service;

receive a second selection of the financial transaction from the multiple types of transactions presented as part of the menu;

receive the financial account identifier via the presentation instrument reader;

transmit a second message comprising the financial account identifier via the settlement network to the host system initiating a financial transaction; and a printer that prints a healthcare eligibility receipt and a financial transaction receipt.

2. The point-of-care device of claim 1, the point-of-care device further comprising:

a magnetic-stripe reader configured to read a magnetic stripe present on a transaction instrument, wherein the magnetic-stripe reader is the presentation instrument reader and the processor-readable instructions that, when executed, cause the one or more processors to receive the healthcare subscriber identifier associated with the patient via the presentation instrument reader comprise processor-readable instructions which, when executed, cause the one or more processors to:

receive, via the magnetic-stripe reader, the identifier associated with the patient from the magnetic stripe of the transaction instrument.

3. The point-of-care device of claim 2, wherein:

the magnetic-stripe reader is configured to obtain the healthcare subscriber identifier associated with the patient from a third track of the magnetic stripe of the transaction instrument; and the first track and second track of the magnetic stripe of the transaction instrument are associated with financial transaction information that comprises the financial account identifier.

4. The point-of-care device of claim 1, wherein the processor-readable instructions that, when executed, cause the one or more processors to transmit the message to the host system initiating the healthcare eligibility transaction comprise processor-readable instructions which, when executed, cause the one or more processors to:

transmit the message to the host system via a credit card processing network, wherein the credit card processing network is the settlement network.

5. The point-of-care device of claim 1, wherein the processor-readable instructions, when executed, further cause the one or more processors to:

assign a first message type to the message initiating the healthcare eligibility transaction; and assign a second message type to the financial transaction, wherein the first message type and the second message type are different and are used by a remote computer system to determine a type of transaction being conducted.

6. The point-of-care device of claim 1, wherein the accepted eligibility receipt further indicates a primary care physician of the patient.

7. A method for conducting a health care transaction, the method comprising:

presenting, by a point-of-care device, a menu allowing selection from multiple types of transactions, the multiple types of transactions comprising: a financial transaction and a healthcare eligibility transaction, wherein presentation of the multiple types of transactions occurs simultaneously and the point-of-care device comprises a presentation instrument reader configured to read a healthcare subscriber identifier and a financial account identifier from a presentation instrument;

presenting, by a point-of-care device, a first option associated with the financial transaction and a second option associated with the healthcare eligibility transaction, wherein the first option and second option are presented simultaneously;

receiving, by the point-of-care device, a selection of the healthcare eligibility transaction from the multiple types of transactions;

receiving, by the point-of-care device via the presentation instrument reader, the healthcare subscriber identifier associated with a patient;

transmitting, by the point-of-care device, via a settlement network, a first message to a host system that comprises the healthcare subscriber identifier initiating the healthcare eligibility transaction;

receiving, by the point-of-care device, via the settlement network, in response to the first message, an accepted eligibility receipt that indicates a co-pay amount corresponding to a healthcare service;

receiving, by the point-of-care device, a second selection of the financial transaction from the multiple types of transactions;

receiving, by the point-of-care device, the financial account identifier via the presentation instrument reader;

transmitting, by the point-of-care device, a second message comprising the financial account identifier via the settlement network to the host system initiating a financial transaction; and print with a printer a healthcare eligibility receipt and a financial transaction receipt.

8. The method for conducting the health care transaction of claim 7, wherein receiving the identifier associated with the patient via the presentation reader comprises:

receiving, via a magnetic-stripe reader of the point-of-care device, the healthcare subscriber identifier associated with the patient from a magnetic stripe of a transaction instrument, wherein the presentation reader comprises the magnetic-stripe reader.

9. The method for conducting the health care transaction of claim 8, wherein the healthcare subscriber identifier associated with the patient is received from a third track of the magnetic stripe of the transaction instrument, the first track and second track comprising financial account information which comprises the financial account identifier.

10. The method for conducting the health care transaction of claim 7, wherein transmitting the message to the host system initiating the healthcare eligibility transaction comprises:

transmitting the message to the host system via a credit card processing network, wherein the credit card processing network is the settlement network.

11. The method for conducting the health care transaction of claim 7, the method further comprising:

assigning, by the point-of-care device, a first message type to the message initiating the healthcare eligibility transaction; and assign, by the point-of-care device, a second message type to the financial transaction, wherein the first message type and the second message type are different and are used by a remote computer system to determine a type of transaction being conducted.

12. The method for conducting the health care transaction of claim 7, wherein the accepted eligibility receipt further indicates a primary care physician of the patient.

13. A non-transitory processor-readable medium comprising processor-readable instructions configured to cause one or more processors of a point-of-care device that comprises a printer, and a presentation instrument reader configured to read a healthcare subscriber identifier and a financial account identifier from a presentation instrument to:

cause presentation of a menu allowing selection from multiple types of transactions, the multiple types of transactions comprising: a financial transaction and a healthcare eligibility transaction;

cause presentation of a first option associated with the financial transaction and a second option associated with the healthcare eligibility transaction, wherein the first option and second option are presented simultaneously;

receive a selection of the healthcare eligibility transaction from the multiple types of transactions presented as part of the menu;

receive the healthcare subscriber identifier associated with a patient, the identifier being received via a presentation instrument reader device;

transmit a first message comprising the healthcare subscriber via a credit card processing network to a host system initiating the healthcare eligibility transaction;

receive, in response to the first message, via the credit card processing network, an accepted eligibility receipt that indicates a co-pay amount corresponding to a healthcare service;

receive a second selection of the financial transaction from the multiple types of transactions presented as part of the menu;

receive the financial account identifier via the presentation instrument reader;

transmit a second message comprising the financial account identifier via the settlement network to the host system initiating a financial transaction; and print with the printer a healthcare eligibility receipt and a financial transaction receipt.

14. The non-transitory processor-readable medium of claim 13, wherein the processor-readable instructions are further configured to cause the one or more processors to:

receive, via a magnetic-stripe reader, the healthcare subscriber identifier associated with the patient from a magnetic stripe of a transaction instrument, wherein the presentation instrument reader device is a magnetic-stripe reader.

15. The non-transitory processor-readable medium of claim 14, wherein the processor-readable instructions configured to cause the one or more processors to receive the identifier comprise processor-readable instructions configured to cause the one or more processors to receive the identifier associated with the patient from a third track of the magnetic stripe of the transaction instrument;

wherein the first track and second track of the magnetic stripe of the transaction instrument are associated with financial transaction information.

* * * * *